(12) United States Patent
Hino et al.

(10) Patent No.: US 11,592,419 B2
(45) Date of Patent: Feb. 28, 2023

(54) SENSOR ELEMENT FOR GAS SENSOR

(71) Applicant: NGK INSULATORS, LTD., Nagoya (JP)

(72) Inventors: Takashi Hino, Kasugai (JP); Ryo Hayase, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 287 days.

(21) Appl. No.: 16/827,753

(22) Filed: Mar. 24, 2020

(65) Prior Publication Data
US 2020/0309732 A1    Oct. 1, 2020

(30) Foreign Application Priority Data
Mar. 29, 2019    (JP) .............................. JP2019-065762

(51) Int. Cl.
*G01N 27/407*    (2006.01)
*G01N 33/00*    (2006.01)

(52) U.S. Cl.
CPC ..... *G01N 27/4077* (2013.01); *G01N 27/4071* (2013.01); *G01N 33/0037* (2013.01)

(58) Field of Classification Search
CPC ........... G01N 27/4077; G01N 27/4071; G01N 33/0037; G01N 27/406–41; G01N 33/0004–0075
See application file for complete search history.

(56) References Cited

U.S. PATENT DOCUMENTS

| | | | |
|---|---|---|---|
| 6,565,723 B1* | 5/2003 | Danley .............. | G01N 27/4077 204/429 |
| 2010/0155240 A1 | 6/2010 | Matsuoka et al. | |
| 2012/0211362 A1* | 8/2012 | Onkawa ............ | G01N 27/4077 204/424 |
| 2014/0291150 A1* | 10/2014 | Otsuka ............... | G01N 27/4077 204/424 |
| 2015/0060274 A1* | 3/2015 | Ishikawa ............ | G01N 27/4077 204/424 |

(Continued)

FOREIGN PATENT DOCUMENTS

| | | | | |
|---|---|---|---|---|
| JP | 2009080099 A | * | 4/2009 | ........ G01N 27/4071 |
| JP | 2010-169655 A | | 8/2010 | |
| JP | 2012-93330 A | | 5/2012 | |

(Continued)

OTHER PUBLICATIONS

Unexamined U.S. Appl. No. 16/827,754, filed Mar. 24, 2020.

(Continued)

*Primary Examiner* — Joshua L Allen
(74) *Attorney, Agent, or Firm* — Mattingly & Malur, PC

(57) ABSTRACT

A sensor element for a gas sensor includes: an element base being a ceramic structure including a sensing part to sense a gas component to be measured; and a leading-end protective layer being a porous layer to surround a predetermined range from a leading end portion on a side of the sensing part of the element base. The leading-end protective layer protrudes at a first end portion thereof opposite to a portion surrounding the element base in a longitudinal direction of the element base. A/B≥1.1 where A is maximum thickness of the leading-end protective layer, and B is thickness of the leading-end protective layer in a base portion that does not protrude.

4 Claims, 3 Drawing Sheets

(56) References Cited

U.S. PATENT DOCUMENTS

2020/0173957 A1\* 6/2020 Mouri ................ G01N 27/4072
2020/0182182 A1\* 6/2020 Imada ................. G01N 33/006

FOREIGN PATENT DOCUMENTS

| JP | 2013-104706 A | 5/2013 | | |
|---|---|---|---|---|
| JP | 5387555 B2 | 1/2014 | | |
| JP | 2019039693 A | \* | 3/2019 | ......... F02D 41/1454 |

OTHER PUBLICATIONS

Unexamined U.S. Appl. No. 16/827,759, filed Mar. 24, 2020.
Third-Party Submission received in corresponding Japanese Application No. 2019-065762 dated Feb. 1, 2022.
Chinese Office Action received in corresponding Chinese Application No. 202010180267.9 dated Jun. 1, 2022.

\* cited by examiner

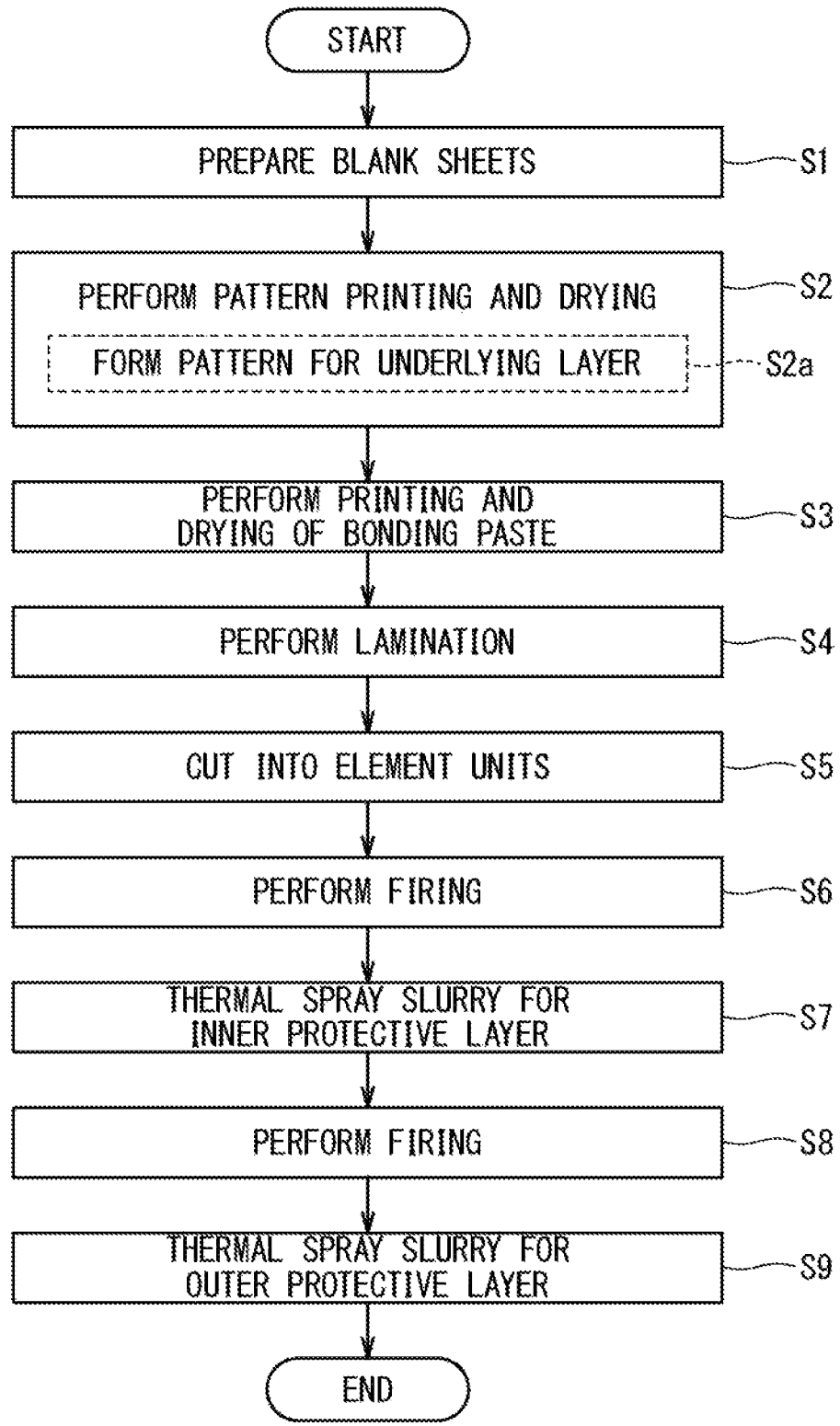

SENSOR ELEMENT FOR GAS SENSOR

CROSS-REFERENCE TO RELATED APPLICATION

The present application claims priority from Japanese application JP2019-065762, filed on Mar. 29, 2019, the contents of which is hereby incorporated by reference into this application.

BACKGROUND OF THE INVENTION

Field of the Invention

The present invention relates to a sensor element for a gas sensor, and, in particular, to a surface protective layer thereof.

Description of the Background Art

As a gas sensor for determining concentration of a desired gas component contained in a measurement gas, such as an exhaust gas from an internal combustion engine, a gas sensor that includes a sensor element made of an oxygen-ion conductive solid electrolyte, such as zirconia ($ZrO_2$), and including some electrodes on the surface and the inside thereof has been widely known. As the sensor element, a sensor element having an elongated planar shape, including a protective layer formed of a porous body (porous protective layer) in an end portion in which a part for introducing the measurement gas is provided, and further including a surface protective layer having a smaller porosity than the porous protective layer outside the porous protective layer has been known (see Japanese Patent No. 5387555, for example).

The protective layer is provided to the surface of the sensor element to secure water resistance of the sensor element when the gas sensor is in use. Specifically, the protective layer is provided to prevent water-induced cracking of the sensor element under the action of thermal shock caused by heat (cold) from water droplets adhering to the surface of the sensor element.

It is found, from intensive studies made by the inventors of the present invention, that, in a case where the protective layer of the sensor element is subjected to thermal shock by adherence of water droplets, stress tends to concentrate along an edge portion of the sensor element, and the protective layer is likely to be separated in the edge portion even though water-induced cracking does not occur.

To increase resistance to such thermal shock (thermal shock resistance), the thickness of a protective layer having large thermal capacity could be increased. In this case, the sensor element can operate even in a state of the protective layer containing a large amount of moisture, but there is a problem in that, as the amount of moisture contained in the sensor element increases, time required to evaporate moisture when the sensor element is heated to start driving increases, and, as a result, the start of operation of a gas sensor is delayed. Furthermore, there is another problem in that cracking of the sensor element occurs due to thermal stress at the start of driving.

SUMMARY

The present invention relates to a sensor element for a gas sensor, and is, in particular, directed to a configuration of a surface protective layer thereof.

According to the present invention, a sensor element for a gas sensor includes: an element base being a ceramic structure including a sensing part to sense a gas component to be measured; and a leading-end protective layer being a porous layer to surround a predetermined range from a leading end portion on a side of the sensing part of the element base, wherein the leading-end protective layer protrudes at a first end portion thereof, the first end portion being an end portion of the leading-end protective layer and opposite to a portion surrounding the leading end portion of the element base in a longitudinal direction of the element base, $A/B \geq 1.1$ where A is maximum thickness of the leading-end protective layer, and B is thickness of the leading-end protective layer in a base portion, and the base portion is a portion of the leading-end protective layer that does not protrude.

Accordingly, time required to evaporate moisture from the sensor element at the start of driving of the gas sensor is thereby reduced. Furthermore, stress acting on the leading-end protective layer at the start of driving is relieved, thereby to suitably suppress the occurrence of cracking of the sensor element.

It is thus an object of the present invention to provide a sensor element for a gas sensor in which, while thermal shock resistance is secured, time to evaporate moisture at the start of driving is reduced, and thermal stress at the start of driving is suitably relieved.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a flowchart of processing at the manufacture of the sensor element 10.

DESCRIPTION OF THE PREFERRED EMBODIMENTS

<Overview of Sensor Element and Gas Sensor>

Figure 1:
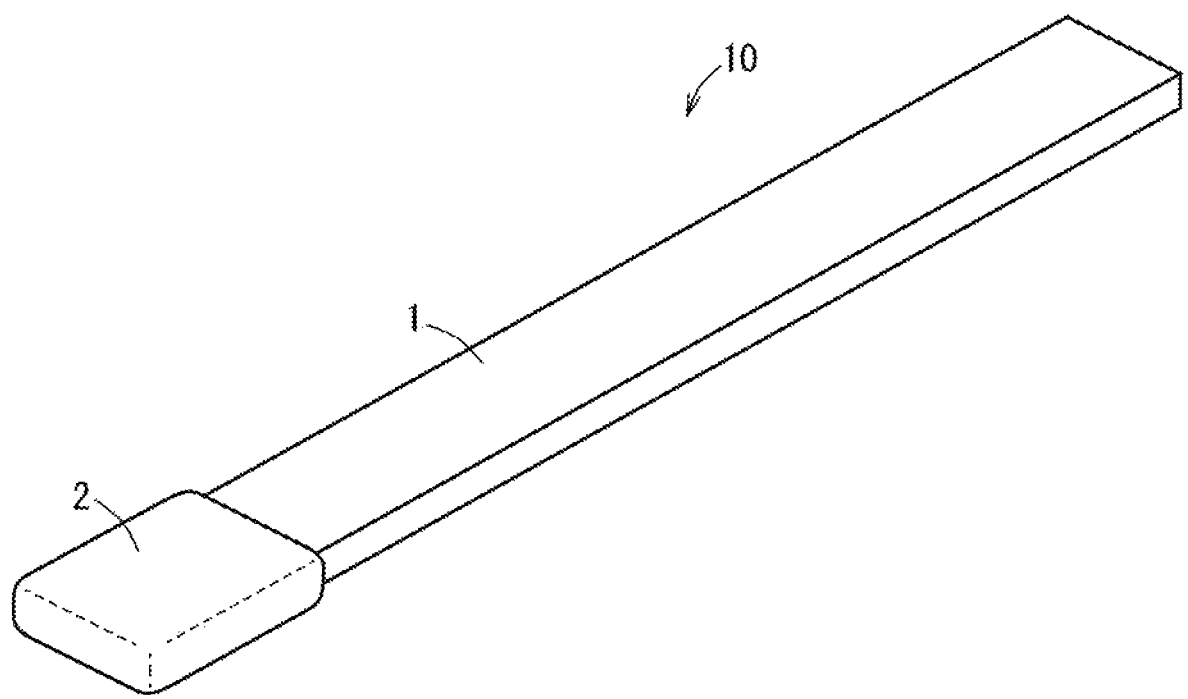
FIG. 1 is a schematic external perspective view of a sensor element 10.
Figure 2:
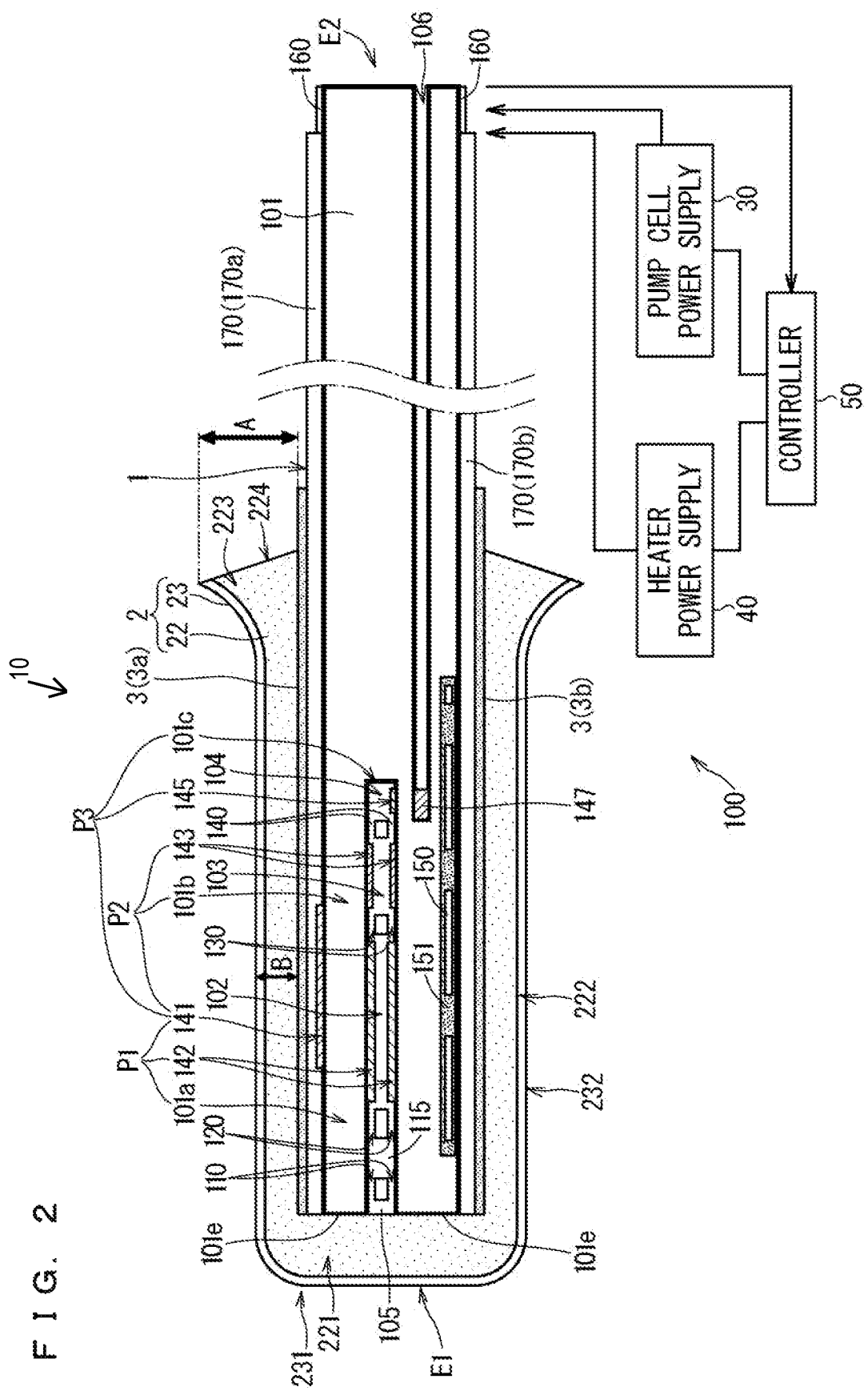
FIG. 2 is a schematic view illustrating a configuration of a gas sensor 100 including a sectional view taken along a longitudinal direction of the sensor element 10.

FIG. 1 is a schematic external perspective view of a sensor element (gas sensor element) 10 according to an embodiment of the present invention. FIG. 2 is a schematic view illustrating a configuration of a gas sensor 100 including a sectional view taken along a longitudinal direction of the sensor element 10. The sensor element 10 is a ceramic structure as a main component of the gas sensor 100 sensing a predetermined gas component in a measurement gas, and measuring concentration thereof. The sensor element 10 is a so-called limiting current gas sensor element.

In addition to the sensor element 10, the gas sensor 100 mainly includes a pump cell power supply 30, a heater power supply 40, and a controller 50.

As illustrated in FIG. 1, the sensor element 10 has a configuration in which one end portion of an elongated planar element base 1 is covered with a porous leading-end protective layer 2.

As illustrated in FIG. 2, the element base 1 includes an elongated planar ceramic body 101 as a main structure, main surface protective layers 170 are provided on two main surfaces of the ceramic body 101, and, in the sensor element 10, the leading-end protective layer 2 is further provided outside both an end surface (a leading end surface 101e of the ceramic body 101) and four side surfaces on one leading end portion. The four side surfaces other than opposite end surfaces in the longitudinal direction of the sensor element 10 (or the element base 1, or the ceramic body 101) are hereinafter simply referred to as side surfaces of the sensor element 10 (or the element base 1, or the ceramic body 101).

The ceramic body 101 is made of ceramic containing, as a main component, zirconia (yttria stabilized zirconia), which is an oxygen-ion conductive solid electrolyte. Various components of the sensor element 10 are provided outside and inside the ceramic body 101. The ceramic body 101 having the configuration is dense and airtight. The configuration of the sensor element 10 illustrated in FIG. 2 is just an example, and a specific configuration of the sensor element 10 is not limited to this configuration.

The sensor element 10 illustrated in FIG. 2 is a so-called serial three-chamber structure type gas sensor element including a first internal chamber 102, a second internal chamber 103, and a third internal chamber 104 inside the ceramic body 101. That is to say, in the sensor element 10, the first internal chamber 102 communicates, through a first diffusion control part 110 and a second diffusion control part 120, with a gas inlet 105 opening to the outside on a side of one end portion E1 of the ceramic body 101 (to be precise, communicating with the outside through the leading-end protective layer 2), the second internal chamber 103 communicates with the first internal chamber 102 through a third diffusion control part 130, and the third internal chamber 104 communicates with the second internal chamber 103 through a fourth diffusion control part 140. A path from the gas inlet 105 to the third internal chamber 104 is also referred to as a gas distribution part. In the sensor element 10 according to the present embodiment, the distribution part is provided straight along the longitudinal direction of the ceramic body 101.

The first diffusion control part 110, the second diffusion control part 120, the third diffusion control part 130, and the fourth diffusion control part 140 are each provided as two slits vertically arranged in FIG. 2. The first diffusion control part 110, the second diffusion control part 120, the third diffusion control part 130, and the fourth diffusion control part 140 provide predetermined diffusion resistance to a measurement gas passing therethrough. A buffer space 115 having an effect of buffering pulsation of the measurement gas is provided between the first diffusion control part 110 and the second diffusion control part 120.

An outer pump electrode 141 is provided on an outer surface of the ceramic body 101, and an inner pump electrode 142 is provided in the first internal chamber 102. Furthermore, an auxiliary pump electrode 143 is provided in the second internal chamber 103, and a measurement electrode 145 as a sensing part to directly sense a gas component to be measured is provided in the third internal chamber 104. In addition, a reference gas inlet 106 which communicates with the outside and through which a reference gas is introduced is provided on a side of the other end portion E2 of the ceramic body 101, and a reference electrode 147 is provided in the reference gas inlet 106.

In a case where a target of measurement of the sensor element 10 is NOx in the measurement gas, for example, concentration of a NOx gas in the measurement gas is calculated by a process as described below.

First, the measurement gas introduced into the first internal chamber 102 is adjusted to have a substantially constant oxygen concentration by a pumping action (pumping in or out of oxygen) of a main pump cell P1, and then introduced into the second internal chamber 103. The main pump cell P1 is an electrochemical pump cell including the outer pump electrode 141, the inner pump electrode 142, and a ceramic layer 101a that is a portion of the ceramic body 101 existing between these electrodes. In the second internal chamber 103, oxygen in the measurement gas is pumped out of the element by a pumping action of an auxiliary pump cell P2 that is also an electrochemical pump cell, so that the measurement gas is in a sufficiently low oxygen partial pressure state. The auxiliary pump cell P2 includes the outer pump electrode 141, the auxiliary pump electrode 143, and a ceramic layer 101b that is a portion of the ceramic body 101 existing between these electrodes.

The outer pump electrode 141, the inner pump electrode 142, and the auxiliary pump electrode 143 are each formed as a porous cermet electrode (e.g., a cermet electrode made of $ZrO_2$ and Pt that contains Au of 1%). The inner pump electrode 142 and the auxiliary pump electrode 143 to be in contact with the measurement gas are each formed using a material having weakened or no reducing ability with respect to a NOx component in the measurement gas.

NOx in the measurement gas caused by the auxiliary pump cell P2 to be in the low oxygen partial pressure state is introduced into the third internal chamber 104, and reduced or decomposed by the measurement electrode 145 provided in the third internal chamber 104. The measurement electrode 145 is a porous cermet electrode also functioning as a NOx reduction catalyst that reduces NOx existing in an atmosphere in the third internal chamber 104. During the reduction or decomposition, a potential difference between the measurement electrode 145 and the reference electrode 147 is maintained constant. Oxygen ions generated by the above-mentioned reduction or decomposition are pumped out of the element by a measurement pump cell P3. The measurement pump cell P3 includes the outer pump electrode 141, the measurement electrode 145, and a ceramic layer 101c that is a portion of the ceramic body 101 existing between these electrodes. The measurement pump cell P3 is an electrochemical pump cell pumping out oxygen generated by decomposition of NOx in an atmosphere around the measurement electrode 145.

Pumping (pumping in or out of oxygen) of the main pump cell P1, the auxiliary pump cell P2, and the measurement pump cell P3 is achieved, under control performed by the controller 50, by the pump cell power supply (variable power supply) 30 applying a voltage necessary for pumping across electrodes included in each of the pump cells. In a case of the measurement pump cell P3, a voltage is applied across the outer pump electrode 141 and the measurement electrode 145 so that the potential difference between the measurement electrode 145 and the reference electrode 147 is maintained at a predetermined value. The pump cell power supply 30 is typically provided for each pump cell.

The controller 50 detects a pump current Ip2 flowing between the measurement electrode 145 and the outer pump electrode 141 in accordance with the amount of oxygen pumped out by the measurement pump cell P3, and calculates a NOx concentration in the measurement gas based on a linear relationship between a current value (NOx signal) of the pump current Ip2 and the concentration of decomposed NOx.

The gas sensor 100 preferably includes a plurality of electrochemical sensor cells, which are not illustrated, sensing the potential difference between each pump electrode and the reference electrode 147, and each pump cell is controlled by the controller 50 based on a signal detected by each sensor cell.

In the sensor element 10, a heater 150 is buried in the ceramic body 101. The heater 150 is provided, below the gas distribution part in FIG. 2, over a range from the vicinity of the one end portion E1 to at least a location of formation of the measurement electrode 145 and the reference electrode 147. The heater 150 is provided mainly to heat the sensor element 10 to enhance oxygen-ion conductivity of the solid electrolyte forming the ceramic body 101 when the sensor element 10 is in use. More particularly, the heater 150 is provided to be surrounded by an insulating layer 151.

The heater 150 is a resistance heating body made, for example, of platinum. The heater 150 generates heat by being powered from the heater power supply 40 under control performed by the controller 50.

The sensor element 10 according to the present embodiment is heated by the heater 150 when being in use so that the temperature at least in a range from the first internal chamber 102 to the second internal chamber 103 becomes 500° C. or more. In some cases, the sensor element 10 is heated so that the temperature of the gas distribution part as a whole from the gas inlet 105 to the third internal chamber 104 becomes 500° C. or more. These are to enhance the oxygen-ion conductivity of the solid electrolyte forming each pump cell and to desirably demonstrate the ability of each pump cell. In this case, the temperature in the vicinity of the first internal chamber 102, which becomes the highest temperature, becomes approximately 700° C. to 800° C. The temperature of the sensor element 10 when the sensor element 10 is in use (is driven) is referred to as element driving temperature.

In the following description, from among the two main surfaces of the ceramic body 101, a main surface (or an outer surface of the sensor element 10 having the main surface) which is located on an upper side in FIG. 2 and on a side where the main pump cell P1, the auxiliary pump cell P2, and the measurement pump cell P3 are mainly provided is also referred to as a pump surface, and a main surface (or an outer surface of the sensor element 10 having the main surface) which is located on a lower side in FIG. 2 and on a side where the heater 150 is provided is also referred to as a heater surface. In other words, the pump surface is a main surface closer to the gas inlet 105, the three internal chambers, and the pump cells than to the heater 150, and the heater surface is a main surface closer to the heater 150 than to the gas inlet 105, the three internal chambers, and the pump cells.

A plurality of electrode terminals 160 are formed on the respective main surfaces of the ceramic body 101 on the side of the other end portion E2 to establish electrical connection between the sensor element 10 and the outside. These electrode terminals 160 are electrically connected to the above-mentioned five electrodes, opposite ends of the heater 150, and a lead for detecting heater resistance, which is not illustrated, through leads provided inside the ceramic body 101, which are not illustrated, to have a predetermined correspondence relationship. Application of a voltage from the pump cell power supply 30 to each pump cell of the sensor element 10 and heating by the heater 150 by being powered from the heater power supply 40 are thus performed through the electrode terminals 160.

The sensor element 10 further includes the above-mentioned main surface protective layers 170 (170*a* and 170*b*) on the pump surface and the heater surface of the ceramic body 101. The main surface protective layers 170 are layers made of alumina, having a thickness of approximately 5 μm to 30 μm, and including pores with a porosity of approximately 20% to 40%, and are provided to prevent adherence of any foreign matter and poisoning substances to the main surfaces (the pump surface and the heater surface) of the ceramic body 101 and the outer pump electrode 141 provided on the pump surface. The main surface protective layer 170*a* on the pump surface thus functions as a pump electrode protective layer for protecting the outer pump electrode 141.

In the present embodiment, the porosity is obtained by applying a known image processing method (e.g., binarization processing) to a scanning electron microscope (SEM) image of an evaluation target.

The main surface protective layers 170 are provided over substantially all of the pump surface and the heater surface except that the electrode terminals 160 are partially exposed in FIG. 2, but this is just an example. The main surface protective layers 170 may locally be provided in the vicinity of the outer pump electrode 141 on the side of the one end portion E1 compared with the case illustrated in FIG. 2.

<Details of Leading-End Protective Layer>

In the sensor element 10, the leading-end protective layer 2 is provided around an outermost periphery of the element base 1 having a configuration as described above in a predetermined range from the one end portion E1.

The leading-end protective layer 2 is provided in a manner of surrounding a portion of the element base 1 in which the temperature becomes high (up to approximately 700° C. to 800° C.) when the gas sensor 100 is in use, in order to secure water resistance in the portion to thereby suppress the occurrence of cracking (water-induced cracking) of the element base 1 due to thermal shock caused by local temperature reduction upon direct exposure of the portion to water.

In addition, the leading-end protective layer 2 is provided to secure poisoning resistance to prevent poisoning substances, such as Mg, from entering into the sensor element 10.

As illustrated in FIG. 2, in the sensor element 10 according to the present embodiment, the leading-end protective layer 2 includes two layers: an inner leading-end protective layer 22 and an outer leading-end protective layer 23. An underlying layer 3 is provided between the leading-end protective layer 2 (the inner leading-end protective layer 22) and the element base 1.

The underlying layer 3 is a layer provided to secure bonding (adhesion) of the inner leading-end protective layer 22 formed thereon (further the outer leading-end protective layer 23). The underlying layer 3 is provided at least on two main surfaces of the element base 1 on a side of the pump surface and a side of the heater surface. That is to say, the underlying layer 3 includes an underlying layer 3*a* on the side of the pump surface and an underlying layer 3*b* on the side of the heater surface. The underlying layer 3, however, is not provided on a side of the leading end surface 101*e* of the ceramic body 101 (of the element base 1).

The underlying layer 3 is made of alumina, has a porosity of 30% to 60%, and has a thickness of 15 μm to 50 μm. In contrast to the inner leading-end protective layer 22 and the outer leading-end protective layer 23, the underlying layer 3 is formed along with the element base 1 in a process of manufacturing the element base 1 as described below.

The inner leading-end protective layer 22 and the outer leading-end protective layer 23 are provided in this order from inside to cover the leading end surface 101*e* and the four side surfaces on the side of the one end portion E1 of the element base 1 (around an outer periphery of the element base 1 on the side of the one end portion E1). A portion of the inner leading-end protective layer 22 on the side of the leading end surface 101e is particularly referred to as a leading-end portion 221, and a portion of the inner leading-end protective layer 22 on the side of the pump surface and the side of the heater surface is particularly referred to as a main surface portion 222. Similarly, a portion of the outer leading-end protective layer 23 on the side of the leading end surface 101e is particularly referred to as a leading-end portion 231, and a portion of the outer leading-end protective layer 23 on the side of the pump surface and the side of the heater surface is particularly referred to as a main surface portion 232. The main surface portion 222 of the inner leading-end protective layer 22 is adjacent to the underlying layer 3.

The inner leading-end protective layer 22 is made of alumina, and has a porosity of 30% to 90%. The outer leading-end protective layer 23 is made of alumina, and has a porosity of 10% to 30%. The leading-end protective layer 2 thereby has roughly such a configuration that the inner leading-end protective layer 22 having low thermal conductivity is covered with the outer leading-end protective layer 23 having a smaller porosity than the inner leading-end protective layer 22.

The inner leading-end protective layer 22 has a protrusion 223 having a larger thickness than the other portions in the vicinity of an end portion opposite the leading-end portion 221. The outer leading-end protective layer 23 is formed to follow the shape of the protrusion 223. The leading-end protective layer 2 as a whole thereby protrudes (has the protrusion) at an end portion located at a predetermined distance from the one end portion E1 of the element base 1. At the end portion, (the protrusion 223 of) the inner leading-end protective layer 22 is not covered with the outer leading-end protective layer 23, and has an end surface 224 externally exposed while being inclined. More particularly, the protrusion 223 is provided to be closer to the other end portion E2 than the gas distribution part provided inside the ceramic body 101 is.

Although the protrusion 223 is triangular in cross section, and the protrusion 223 and the outer leading-end protective layer 23 form a single cross section in FIG. 2, the protrusion 223 is not necessarily provided in this manner. The protrusion 223 may be provided in another manner as long as the leading-end protective layer 2 has the protrusion 223, and the end surface 224 thereof is externally exposed to have a sufficient area.

Furthermore, the leading-end protective layer 2 has a maximum thickness A in the vicinity of the protrusion 223 of 1.1 times or more thickness (hereinafter, base thickness) B in a portion (base portion) other than the protrusion 223 on the side of the pump surface, which is typified by the thickness above the inner pump electrode 142. That is to say, the leading-end protective layer 2 is provided so that $A/B \geq 1.1$.

Such a configuration of the leading-end protective layer 2 has an effect of reducing time required to evaporate moisture from the sensor element 10 at the start of operation of the gas sensor 100 compared with a case where the leading-end protective layer 2 is configured to have uniform thickness (so that $A/B=1.0$). Specifically, when the temperature of the sensor element 10 becomes a high temperature of up to 700° C. to 800° C. during its use, moisture (water vapor) resulting from water droplets adhering to the surface of the leading-end protective layer 2 (the surface of the outer leading-end protective layer 23) enters into the leading-end protective layer 2, that is, into the inner leading-end protective layer 22 through the outer leading-end protective layer 23, but a part of it condenses as the sensor element 10 is cooled after use, and returns to the water droplets again to remain in the leading-end protective layer 2. Moisture remaining in the leading-end protective layer 2 as described above evaporates when the sensor element 10 is heated by the heater 150 to be started to be used again, and is externally discharged as water vapor.

In this case, by providing the protrusion 223 so that $A/B \geq 1.1$, and the end surface 224 of the inner leading-end protective layer 22 having a large porosity is externally exposed to be inclined along the protrusion 223 having a larger thickness than the other portions as described above, moisture is preferentially discharged from the end surface 224 through the inner leading-end protective layer 22 having a large porosity, not through the outer leading-end protective layer 23 having a small porosity. As a result, in the sensor element 10, the time required to evaporate moisture from the sensor element 10 at the start of operation of the gas sensor 100 is reduced.

Such an effect of reducing the time required for evaporation can be confirmed by evaluating the evaporation time when a predetermine amount of water is absorbed into the surface of the leading-end protective layer 2 in a state of heating the sensor elements 10.

The protrusion 223 also has an effect of relieving stress acting on the leading-end protective layer 2 at the start of driving of the sensor element 10 (when the temperature of the sensor element 10 is increased by the heater 150 to be the element driving temperature) compared with the case where the leading-end protective layer 2 is configured to have uniform thickness (so that $A/B=1.0$). The effect of relieving stress can be evaluated, for example, by the magnitude of statistical probability of the occurrence of cracking at the start of driving.

To suitably obtain these effects, the inner leading-end protective layer 22 preferably has a thickness of 50 μm to 1500 μm in a portion providing the base thickness B, the outer leading-end protective layer 23 preferably has a thickness of 20 μm to 300 μm in the portion, and the base thickness B is preferably 300 μm or more.

The effects, however, can be obtained in the sensor element 10 in which $A/B=1.0$ if the base thickness B is approximately 300 μm, so that the effects have greater technical significance in a case where the base thickness B is sufficiently larger than 300 μm.

For example, in the case that the base thickness B is 1200 μm or more and $A/B=1.0$, thermal stress acting on the sensor element 10 increases to frequently cause cracking of the sensor element 10, upon heating of the sensor element 10 as a whole including the leading-end protective layer 2 by the heater 150 to start use of the gas sensor 100, but the occurrence of such cracking is suitably suppressed when $A/B \geq 1.1$.

The inner leading-end protective layer 22 and the outer leading-end protective layer 23 are formed by sequentially thermal spraying (plasma-spraying) materials for them with respect to the element base 1 having a surface on which the underlying layer 3 has been formed. This is to develop an anchoring effect between the inner leading-end protective layer 22 and the underlying layer 3 formed in advance in the process of manufacturing the element base 1 to thereby secure bonding (adhesion) of the inner leading-end protective layer 22 (including the outer leading-end protective layer 23 formed outside the inner leading-end protective layer 22) to the underlying layer 3. In other words, this means that the underlying layer 3 has a function to secure bonding (adhesion) of the inner leading-end protective layer 22. Secured bonding (adhesion) in this manner contributes to suppression of separation of the leading-end protective layer 2 from the element base 1 caused by thermal shock due to adherence of water droplets.

The inner leading-end protective layer 22 and the outer leading-end protective layer 23 are provided not to cover the underlying layer 3 (3*a* and 3*b*) as a whole but to expose an end portion of the underlying layer 3 on a side opposite the side of the one end portion E1 in the longitudinal direction of the sensor element 10. This is to more surely secure bonding (adhesion) of the inner leading-end protective layer 22 (including the outer leading-end protective layer 23 formed outside the inner leading-end protective layer 22) to the underlying layer 3.

As described above, in the sensor element 10 according to the present embodiment, the leading-end protective layer 2 provided to surround the portion of the element base 1 in which the temperature becomes high when the gas sensor 100 is in use in order to secure thermal shock resistance includes the two layers: the inner leading-end protective layer 22 and the outer leading-end protective layer 23 having a smaller porosity than the inner leading-end protective layer, and the protrusion 223 is provided at the end portion on the side opposite the side of the one end portion E1 of the element base so that the end surface 224 of the protrusion is exposed while being inclined. Furthermore, the leading-end protective layer is configured so that the maximum thickness A and the base thickness B satisfy A/B≥1.1. With this configuration, in the sensor element 10, the time required to evaporate moisture at the start of driving of the gas sensor 100 is reduced. Furthermore, stress acting on the leading-end protective layer 2 at the start of driving is relieved, thereby to suitably suppress the occurrence of cracking of the sensor element 10.

<Process of Manufacturing Sensor Element>

One example of a process of manufacturing the sensor element 10 having a configuration and features as described above will be described next. FIG. 3 is a flowchart of processing at the manufacture of the sensor element 10.

At the manufacture of the element base 1, a plurality of blank sheets (not illustrated) being green sheets containing the oxygen-ion conductive solid electrolyte, such as zirconia, as a ceramic component and having no pattern formed thereon are prepared first (step S1).

The blank sheets have a plurality of sheet holes used for positioning in printing and lamination. The sheet holes are formed to the blank sheets in advance prior to pattern formation through, for example, punching by a punching machine. Green sheets corresponding to a portion of the ceramic body 101 in which an internal space is formed also include penetrating portions corresponding to the internal space formed in advance through, for example, punching as described above. The blank sheets are not required to have the same thickness, and may have different thicknesses in accordance with corresponding portions of the element base 1 eventually formed.

After preparation of the blank sheets corresponding to the respective layers, pattern printing and drying are performed on the individual blank sheets (step S2). Specifically, a pattern of various electrodes, a pattern of the heater 150 and the insulating layer 151, a pattern of the electrode terminals 160, a pattern of the main surface protective layers 170, a pattern of internal wiring, which is not illustrated, and the like are formed. Application or placement of a sublimable material (vanishing material) for forming the first diffusion control part 110, the second diffusion control part 120, the third diffusion control part 130, and the fourth diffusion control part 140 is also performed at the time of pattern printing. In addition, a pattern to form the underlying layer 3 (3*a* and 3*b*) is printed onto blank sheets to become an uppermost layer and a lowermost layer after lamination (step S2*a*).

The patterns are printed by applying pastes for pattern formation prepared in accordance with the properties required for respective formation targets onto the blank sheets using known screen printing technology. At formation of the underlying layer 3, for example, an alumina paste that can form the underlying layer 3 having a desired porosity and thickness in the sensor element 10 eventually obtained is used. A known drying means can be used for drying after printing.

After pattern printing on each of the blank sheets, printing and drying of a bonding paste are performed to laminate and bond the green sheets (step S3). The known screen printing technology can be used for printing of the bonding paste, and the known drying means can be used for drying after printing.

The green sheets to which an adhesive has been applied are then stacked in a predetermined order, and the stacked green sheets are crimped under predetermined temperature and pressure conditions to thereby form a laminated body (step S4). Specifically, crimping is performed by stacking and holding the green sheets as a target of lamination on a predetermined lamination jig, which is not illustrated, while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be determined appropriately to achieve good lamination. The pattern to form the underlying layer 3 may be formed on the laminated body obtained in this manner.

After the laminated body is obtained as described above, the laminated body is cut out at a plurality of locations to obtain unit bodies eventually becoming the individual element bases 1 (step S5).

The unit bodies as obtained are then each fired at a firing temperature of approximately 1300° C. to 1500° C. (step S6). The element base 1 having main surfaces on which the underlying layer 3 is provided is thereby manufactured. That is to say, the element base 1 is generated by integrally firing the ceramic body 101 made of the solid electrolyte, the electrodes, and the main surface protective layers 170 along with the underlying layer 3. Integral firing is performed in this manner, so that the electrodes each have sufficient adhesion strength in the element base 1.

After the element base 1 is manufactured in the above-mentioned manner, the inner leading-end protective layer 22 and the outer leading-end protective layer 23 are formed with respect to the element base 1. The inner leading-end protective layer 22 is formed by thermal spraying slurry (alumina slurry) for forming the inner leading-end protective layer prepared in advance at a location of the element base 1 as a target of formation of the inner leading-end protective layer 22 to have an intended thickness (step S7), and then firing the element base 1 on which an applied film has been formed in the above manner (step S8). The alumina slurry for forming the inner leading-end protective layer contains alumina powder having predetermined particle size distribution and a pore-forming material at a ratio corresponding to a desired porosity, and the pore-forming material is pyrolyzed by firing the element base 1 after thermal spraying to suitably form the inner leading-end protective layer 22 having a high porosity of 30% to 90%.

Known technology is applicable to thermal spraying and firing, and the protrusion 223 in a desired form can be formed without any particular problems by suitably adjusting a position of the element base 1 at thermal spraying.

Upon formation of the inner leading-end protective layer 22, slurry (alumina slurry) for forming the outer leading-end protective layer similarly prepared in advance and containing alumina powder having predetermined particle size distribution is thermal sprayed at a location of the element base 1 as a target of formation of the outer leading-end protective layer 23 to have an intended thickness (step S9) to thereby form the outer leading-end protective layer 23 having a desired porosity. The alumina slurry for forming the outer leading-end protective layer does not contain the pore-forming material. Known technology is also applicable to the thermal spraying.

The sensor element 10 is obtained by the above-mentioned procedures. The sensor element 10 thus obtained is housed in a predetermined housing, and built into the body (not illustrated) of the gas sensor 100.

<Modifications>

The above-mentioned embodiment is targeted at a sensor element having three internal chambers, but the sensor element is not necessarily required to have a three-chamber structure. That is to say, the sensor element may have one internal chamber or two internal chambers.

Examples

Seven types of sensor elements 10 (Samples No. 1, No. 3, No. 5, No. 7, No. 9, No. 11, and No. 13) having different values of the base thickness (film thickness) B of the leading-end protective layer 2, and having the maximum thickness (A) greater than the base thickness (film thickness) B (so that A/B>1.0) due to the protrusion 223 of the inner leading-end protective layer 22 were manufactured. More specifically, A/B<1.1 only in the sample No. 13, and A/B>1.1 in the other samples. Seven types of sensor elements 10 (Samples No. 2, No. 4, No. 6, No. 8, No. 10, No. 12, and No. 14) not having the protrusion 223, and having uniform thickness of the leading-end protective layer 2 as a whole (i.e., the maximum thickness A=the base thickness B) having the same values as those of the base thickness B in the samples No. 1, No. 3, No. 5, No. 7, No. 9, No. 11, and No. 13 were also manufactured. In each of the sensor elements 10 in the samples No. 1 to No. 14, the end surface 224 of the inner layer 22 was not covered with the outer leading-end protective layer 23, and was externally exposed.

The inner layer 22 and the outer layer 23 were each made of alumina. In each of the samples, the outer layer 23 had a thickness of at least 100 μm to 300 μm.

For each of the sensor elements 10 as obtained, water of 10 μL was similarly dropped, and infiltrated into the leading-end protective layer 2 before driving, and then time required to evaporate infiltrated water at the start of driving (the start of heating by the heater 150) was evaluated (Evaluation 1).

For each of the sensor elements 10, the extent to which thermal stress acting at driving was relieved was evaluated (Evaluation 2).

The base thickness (film thickness) B, the maximum thickness (film thickness) A, a ratio A/B, and the results of Evaluation 1 and Evaluation 2 are shown for each of the samples in Table 1 as a list.

As for Evaluation 1, time from the start of driving of the sensor element 10 including the leading-end protective layer 2 into which water is infiltrated until a voltage output duty ratio of the heater 150 reaches a value at steady control when driving is performed without infiltrating water is defined as the time required to evaporate water. Evaporation time of less than 1 sec is determined to be sufficiently short, and a circle is marked in Table 1 for each of the samples applied thereto. Evaporation time of 1 sec or more and less than 5 sec is determined to be in an allowable range, and a triangle is marked in Table 1 for each of the samples applied thereto. On the other hand, a cross is marked in Table 1 for each of the samples having evaporation time of 5 sec or more.

Furthermore, as for Evaluation 2, the extent to which stress on the leading-end protective layer 2 is relieved is determined by a ratio (statistical probability) of the number of sensor elements 10 cracked when the temperature is increased by the heater 150 after the start of driving among many sensor elements 10 manufactured under the same conditions. A ratio of less than 5% is determined to indicate a great effect, and a circle is marked in Table 1 for each of the samples applied thereto. A ratio of 5% or more and less than 20% is determined to indicate a moderate effect, and a triangle is marked in Table 1 for each of the samples applied thereto. On the other hand, a ratio of more than 20% is determined to indicate no effect, and a cross is marked in Table 1 for each of the samples applied thereto.

TABLE 1

| SAMPLE NO. | BASE FILM THICKNESS B (μm) | MAXIMUM FILM THICKNESS A (μm) | RATIO A/B | EVALUATION 1 | EVALUATION 2 |
|---|---|---|---|---|---|
| 1 | 306 | 554 | 1.81 | ○ | ○ |
| 2 | 306 | 306 | 1.00 | ○ | ○ |
| 3 | 460 | 1000 | 2.17 | ○ | ○ |
| 4 | 460 | 460 | 1.00 | Δ | Δ |
| 5 | 644 | 1128 | 1.75 | Δ | ○ |
| 6 | 644 | 644 | 1.00 | Δ | Δ |
| 7 | 1087 | 1696 | 1.56 | Δ | ○ |
| 8 | 1087 | 1087 | 1.00 | x | Δ |
| 9 | 1232 | 1821 | 1.48 | Δ | Δ |
| 10 | 1232 | 1232 | 1.00 | x | x |
| 11 | 1473 | 1875 | 1.27 | Δ | ○ |
| 12 | 1473 | 1473 | 1.00 | x | x |
| 13 | 300 | 320 | 1.07 | ○ | ○ |
| 14 | 300 | 300 | 1.00 | ○ | ○ |

As shown in Table 1, as for Evaluation 1, although the evaporation time was determined to be 5 sec or more in each of the samples No. 8, No. 10, and No. 12 each having a ratio A/B of the maximum thickness A to the base thickness B of 1.0, the evaporation time was less than 5 sec in the other samples.

As for Evaluation 2, samples other than the samples No. 10 and No. 12 having a ratio A/B of 1.0 and having a large value of the base thickness B of 1200 μm or more were determined to have at least moderate effects of relieving stress.

More particularly, for each of the samples No. 1 and No. 13 having a value of the base thickness B of approximately 300 μm from among the samples having a ratio A/B of more than 1.0 as well as the samples (No. 2 and No. 14) corresponding thereto having a ratio A/B of 1.0, the circle is marked in each of Evaluation 1 and Evaluation 2, while the samples No. 3, No. 5, No. 7, No. 9, and No. 11 each having a value of the base thickness B of 400 μm or more, which is sufficiently greater than 300 μm, and having a ratio A/B of 1.1. or more receive higher evaluation than the samples (No. 4, No. 6, No. 8, No. 10, and No. 12) corresponding thereto having a ratio A/B of 1.0 in at least one of Evaluation 1 and Evaluation 2.

The results show that, in a case where the leading-end protective layer 2 is provided in the sensor element 10 to have a value of the base thickness B sufficiently greater than 300 μm, $A/B \geq 1.1$ is effective in reducing the time required to evaporate water and relieving stress at the start of operation of the gas sensor 100.

In particular, comparison between results of evaluation of the samples (No. 10 and No. 12) having values of the base thickness B of more than 1200 μm and each having a ratio A/B of 1.0 and results of evaluation of the samples No. 9 and No. 11 having the same values of the base thickness B and each having a ratio A/B of 1.1. or more shows that the latter receives greater results in each of Evaluation 1 and Evaluation 2 than the former. This suggests that the leading-end protective layer 2 provided so that $A/B \geq 1.1$ is effective in a case where the leading-end protective layer 2 has a greater value of the base thickness B.

While the invention has been shown and described in detail, the foregoing description is in all aspects illustrative and not restrictive. It is therefore understood that numerous modifications and variations can be devised without departing from the scope of the invention.

What is claimed is:

1. A sensor element for a gas sensor comprising:
    an element base being a ceramic structure having a measurement gas inlet at a leading end portion and including a sensing part to sense a gas component to be measured; and
    a leading-end protective layer being a porous layer to surround a predetermined range of said element base from said leading end portion on a side of said sensing part of said element base, wherein
    said leading-end protective layer protrudes at only a first end portion thereof, said first end portion being an end portion of said leading-end protective layer opposite to a portion of said leading-end protective layer surrounding said measurement gas inlet and said leading end portion of said element base in a longitudinal direction of said element base,
    $A/B \geq 1.1$ where A is maximum thickness of said leading-end protective layer, and B is thickness of said leading-end protective layer in a base portion, and
    said base portion is a portion of said leading-end protective layer that does not protrude.

2. The sensor element according to claim 1, wherein said leading-end protective layer includes:
    an inner leading-end protective layer having a porosity of 30% to 90%; and
    an outer leading-end protective layer having a porosity of 10% to 30%,
    said inner leading-end protective layer has a protrusion so that said leading-end protective layer protrudes at said first end portion, and
    said inner leading-end protective layer is externally exposed at said first end portion of said leading-end protective layer.

3. The sensor element according to claim 2, wherein said base portion has a thickness of 300 μm or more,
    said inner leading-end protective layer has a thickness of 50 μm to 1500 μm in said base portion, and
    said outer leading-end protective layer has a thickness of 20 μm to 300 μm in said base portion.

4. The sensor element according to claim 3, wherein said base portion has a thickness of 400 μm or more.

* * * * *